United States Patent
Herzog et al.

(10) Patent No.: US 6,646,155 B2
(45) Date of Patent: Nov. 11, 2003

(54) METHOD FOR PRODUCING ESTERS OF α, β-UNSATURATED CARBOXYLIC ACIDS

(75) Inventors: Reinhard Herzog, Ludwigshafen (DE); Gerhard Nestler, Ludwigshafen (DE); Jürgen Schröder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/181,966

(22) PCT Filed: Feb. 16, 2001

(86) PCT No.: PCT/EP01/01754

§ 371 (c)(1),
(2), (4) Date: Aug. 5, 2002

(87) PCT Pub. No.: WO01/60779

PCT Pub. Date: Aug. 23, 2001

(65) Prior Publication Data

US 2003/0013906 A1 Jan. 16, 2003

(30) Foreign Application Priority Data

Feb. 17, 2000 (DE) .......................................... 100 07 213

(51) Int. Cl.$^7$ ............................ C07C 67/02; C07C 67/48
(52) U.S. Cl. ...................... 560/217; 560/218; 560/203; 560/205
(58) Field of Search .............................. 560/217, 218, 560/203, 205

(56) References Cited

U.S. PATENT DOCUMENTS

| | | |
|---|---|---|
| 2,917,538 A | 12/1959 | Carlyle |
| 3,868,410 A | 2/1975 | Horlenko et al. |
| 4,280,009 A | 7/1981 | Erpenbach et al. |
| 4,280,010 A | 7/1981 | Erpenbach et al. |
| 4,675,436 A * | 6/1987 | Dietrich et al. .............. 560/217 |
| 5,093,520 A * | 3/1992 | Nestler et al. .............. 560/217 |
| 5,386,052 A | 1/1995 | Sakakura |
| 5,659,072 A * | 8/1997 | Bessalem et al. ............ 560/218 |

FOREIGN PATENT DOCUMENTS

DE  195 36 191  4/1997

OTHER PUBLICATIONS

"Acrylic acid and derivatives" Encyclopedia of Chemical Technology, 3$^{rd}$ Edition, vol. 1, pp. 341–342 and pp. 347–348 John Wilet & Sons, New York.

Wolfgang Gerhartz et al, eds.: "Acrylic acid and derivatives" Ullmann's Encyclopedia of Industrial Chemistry, 5$^{th}$ Edition, vol. A1, pp. 168–169 1985.

O. Bayer et al.: "Methoden der organischen chemie" Georg Thieme Verlag Stuttgart, pp. 534–536 1952.

* cited by examiner

*Primary Examiner*—Alan L. Rotman
*Assistant Examiner*—Héctor M Reyes
(74) *Attorney, Agent, or Firm*—Oblon, Spivak, McClelland, Maier & Neustadt, P.C.

(57) ABSTRACT

An ester of an α,β-unsaturated carboxylic acid is prepared by reacting the carboxylic acid with a $C_6$–$C_{12}$-alkanol, cyclopentanol or cyclohexanol in the presence of an acidic esterification catalyst and of an entraining agent for removing the water of reaction formed in the esterification, by a process in which the entraining agent used is the olefin on which the alkanol is based.

16 Claims, No Drawings

METHOD FOR PRODUCING ESTERS OF α, β-UNSATURATED CARBOXYLIC ACIDS

BACKGROUND OF THE INVENTION

1. Field of the Invention

The present invention relates to a process for the preparation of esters of an α,β-unsaturated carboxylic acid by reacting the carboxylic acid with an alkanol in the presence of an acidic esterification catalyst and in the presence of an entraining agent with which the water of reaction formed during the esterification is removed from the esterification process.

2. Description of the Background

The preparation of alkyl esters of α,β-unsaturated carboxylic acids is generally known. It is usually carried out by esterifying the acids with the corresponding alcohol at elevated temperatures in the liquid phase with or without a solvent and in the presence of a strong acid as a catalyst (cf. for example DE-A-23 39 519). In order to avoid polymerization, polymerization inhibitors are generally added. Of particular industrial importance is the esterification of (meth)acrylic acid. The term (meth)acrylic acid denotes acrylic or methacrylic acid in the known manner.

The disadvantage of the esterification processes of the prior art is that, under the esterification conditions, unconverted starting alcohol and unconverted carboxylic acid undergo addition at the double bond of already formed alkyl carboxylate as secondary reactions (Michael addition). Multiple addition is also possible. Furthermore, mixed types may occur. These adducts are alkoxy esters and acyloxy esters and they are referred to briefly as oxyesters. Typical of the oxyesters is the fact that their boiling point is above the boiling points of starting acid, starting alcohol, desired ester formed and any organic solvent present. In the production of the desired ester, they are therefore obtained as a residue and result in considerable reductions in yield. There have therefore been numerous attempts to recover at least a part of the compounds used or the desired ester from the oxyesters (cf. for example DE-A-195 36 191 and the prior art mentioned therein).

In the cleavage process of DE 195 36 191, a considerable amount of olefins is formed, which cannot be further used in the esterification process and therefore has to be separated off and removed.

A further disadvantage of the conventional esterification processes is a consequence of the fact that the ester formation is based on an equilibrium reaction. In order to obtain economical conversions, as a rule a starting material is used in excess and/or the water of esterification formed and/or the desired ester are removed from the equilibrium. In order to shift the equilibrium in the direction of ester formation, an organic entraining agent which forms an azeotropic mixture with water is frequently added. In particular the esterification with higher alkanols is carried out in the presence of an entraining agent for the water of reaction (Kirk-Othmer, "Encyclopedia of Chemical Technology", Vol. 1, page 347, Ullmann's Encyclopedia of Industrial Chemistry, 5th Ed., 1985, Vol. A1, 168; U.S. Pat. Nos. 2,917,538, 5,386,052). Preferably, inert hydrocarbons, e.g. cyclohexane, hexane, benzene and toluene, are used.

The addition of a further "foreign" solvent is however disadvantageous since it has to be separated off separately and, if necessary, purified before being recycled.

DE 2 548 561 therefore proposes separating off the water of reaction formed in the reaction of acrylic acid with ethylhexanol as an azeotropic mixture with ethylhexanol. According to the example, ethylhexanol is used in excess relative to acrylic acid (1:1.42). The disadvantage here is that the esterification has to be carried out under reduced pressure and a residue of about 8% by weight, based on the desired ester, is obtained and has to be disposed of. The process thus causes environmental pollution and is uneconomical.

Influencing the esterification equilibrium by using a larger excess of a starting material (alkanol or carboxylic acid) leads to the formation of byproducts, e.g. ethers and olefins from the alkanol used and acyloxyesters and alkoxyesters by Michael addition of the alkanol or of the carboxylic acid. This is described, for example for acrylic acid, in U.S. Pat. No. 4,280,010 and in DE-A-2 339 519. These byproducts have to be separated off and disposed of in an expensive manner, which is uneconomical and pollutes the environment.

Even without the use of a relatively large excess of alcohol, some of the esters and the alcohol are cleaved under the strongly acidic esterification conditions and olefins are formed, as described, for example, in DE-A-195 36 191 and Houben-Weyl, Methoden der Organischen Chemie, Volume VIII/3, 1952, page 534.

Most processes of the prior art therefore have in common the disadvantage that undesired byproducts have to be separated off and that an additional solvent is required as an entraining agent for removing the water of esterification.

SUMMARY OF THE INVENTION

It is an object of the present invention to provide an esterification process which is simple to carry out and in which the formation of undesired byproducts is reduced.

We have found, surprisingly, that this object is achieved if the olefin which is formed by the elimination of water from the alkanol used for the esterification is used as an entraining agent.

The present invention therefore relates to a process for the preparation of an ester of an α,β-unsaturated carboxylic acid by reacting the carboxylic acid with an alcohol which is selected from $C_6$–$C_{12}$-alkanols, cyclopentanol and cyclohexanol, in the presence of an acidic esterification catalyst and of an entraining agent for removing the water of reaction formed in the esterification, wherein the entraining agent used is the olefin on which the alcohol is based, i.e. an olefin which corresponds to an olefin obtainable by eliminating water from the alcohol employed is used.

DETAILED DESCRIPTION OF THE PREFERRED EMBODIMENTS

With the exception of the entraining agent used, the novel esterification process is carried out in a conventional manner. Suitable processes are described, for example, in Ullmann's Encyclopedia of Industrial Chemistry, 5th Ed., 1985, Vol. A1, 168, 169; Kirk-Othmer, Encyclopedia of Chemical Technology, Vol. 1, pages 341–348; U.S. Pat. Nos. 2,917, 538; 5,385,052. The processes are described using acrylic acid as an example, but the novel process is not restricted to acrylic acid. The esters of other α,β-unsaturated carboxylic acids can be prepared analogously.

The esterifications are typically carried out at from about 80 to 160° C., preferably from 90 to 130° C., and in the presence of an acidic esterification catalyst, for example a mineral acid, a sulfonic acid or phosphoric acid. Sulfuric acid and sulfonic acids are particularly suitable, especially p-toluenesulfonic, benzenesulfonic, dodecylbenzenesulfonic and methanesulfonic acid. The amount of catalyst is from about 0.1 to 10, preferably from 0.5 to 5, % by weight, based on the other starting materials. The esterification is usually also carried out in the presence of an inhibitor which inhibits the polymerization of the carboxylic acid and/or of the ester. Particularly suitable inhibitors are hydroquinone, hydroquinone monomethyl ether, p-methoxyphenol, p-benzoquinone, phenothiazine, 4-hydroxy-2,2,6,6-tetramethyl-1-oxylpiperidine and methylene blue, which are used for stabilization in amounts of from about 200 to 2,000 ppm, based on the weight of the starting materials. The novel process is however not restricted to specific catalysts or inhibitors, and the acid:alcohol ratios, the pressure prevailing during the esterification and the reaction time also play just as minor a role. A typical molar alcohol:acid ratio is from about 1:0.7 to 1:1.2, and typical reaction times are from about 1 to 10, preferably from about 1 to 6, hours. The esterification can be carried out at atmospheric, superatmospheric or reduced pressure and both continuously and batchwise.

Suitable apparatuses for carrying out the esterification and isolating the desired ester from the reaction mixture are conventional units as described, for example, in Ullmann's Encyclopedia of Industrial Chemistry, 5th Ed., 1985, Volume A1, pages 168, 169, and Kirk-Othmer, "Encyclopedia of Chemical Technology", Vol. 1, pages 341, 342.

Alcohol, acid, catalyst and, if desired, polymerization inhibitor are introduced continuously or batchwise into a reactor, for example a simple heatable kettle.

The olefin on which the alcohol used is based (or the parent olefins) is (are), as mentioned, formed as a byproduct in the esterification and the working up.

The amount of olefin formed is dependent on the reaction procedure and the starting substances. In continuous operation, the amount of olefin is, if required, kept constant by removal.

During the formation of the olefins by elimination of water from the alkanol used for the esterification, by cleavage of the ester under the esterification conditions or by cleavage of the oxyesters, in many cases it is not only an olefin which is formed but, as a result of isomerization, a mixture of two or more olefins, depending on the alcohol used. For example, when the alcohol used is 2-ethylhexan-1-ol, it is not only 2-ethylhex-1-ene which is formed but a mixture of isomeric octenes which contains 2-ethylhex-2-ene and 3-methylhept-2-ene as main components. The proportion of the components depends on the reaction conditions.

Accordingly, according to the invention the term "the olefin on which the alcohol is based" is to be understood as meaning not only a (single) olefin but also a mixture of two or more isomeric olefins.

The azeotropic mixture distilled off from the reactor and containing the olefin as entraining agent may also contain certain amounts of desired ester and/or starting alcohol and/or starting acid. The amounts are dependent on the reaction procedure and on the type of acid used and on the alcohol used. The water separates out from the azeotropic mixture distilled off and is removed. The organic phase which contains the olefin can be recycled together with the other components of the mixture, if present, directly to the esterification reaction. This feed can be effected continuously or batchwise. The water which is separated out can be subjected to further working up in order to obtain, for example, desired ester contained therein and/or to recover starting compounds, which can be recycled to the esterification reaction. Moreover, the aqueous phase can be used as wash liquid in one of the wash processes which may be provided for working up the esterification mixture. If desired, the olefin phase too can be treated in order to remove ester or other products contained therein before the olefin is recycled to the esterification reactor. However, the simplest and most economical and therefore preferred procedure comprises directly recycling the entraining agent together with impurities contained therein, such as desired ester and/or starting alcohol and/or starting acid, possibly also with other byproducts, to the esterification reactor.

The esterification reaction mixture in the novel process for esterifying an α,β-unsaturated carboxylic acid is worked up in a conventional manner, i.e. unconverted starting compounds and the desired ester are separated from the reaction mixture by distillation, the acid catalyst used for the esterification being separated off, if necessary, beforehand by extraction by means of water and/or aqueous alkali (cf. for example Ullmann's Encyclopedia of Industrial Chemistry, Vol. A1, 5th Ed., VCH, page 167 et seq.). The working up can be carried out after the end of the esterification reaction, but it is also possible to remove reaction mixture continuously and to work it up. The bottom product remaining during the working up of the esterification reaction mixture by distillation contains the oxyesters. The bottom product can be subjected to a treatment for recovering starting substances and/or for obtaining desired ester, the process described in DE-A-195 36 191 preferably being used. The olefin obtained can be used as an entraining agent. The cleavage products are preferably recycled to the esterification reactor.

In the process according to DE 195 36 191, the bottom product to be cleaved is removed continuously or batchwise from the working up of the esterification mixture by distillation and is fed with the cleavage catalyst to the cleavage reactor. Also possible is a semicontinuous reaction procedure in which the product to be cleaved is fed continuously to the cleavage reactor which contains the cleavage catalyst, and the bottom product is removed batchwise from the cleavage reactor only after the end of the cleavage. The cleavage products are separated off continuously by distillation. The cleavage is preferably carried out in the presence of acid at from about 150 to 250° C. and at a pressure such that the cleavage products formed from the oxyesters vaporize. Preferably, the process is carried out in the presence of molecular oxygen. Regarding the exact manner for carrying out the process, reference may be made to DE-A-19 536 191.

The cleavage products contain, in addition to the desired ester, starting carboxylic acid and starting alcohol, a considerable amount of olefins, for example up to about 20% by weight of octenes in the case of the cleavage of the residue from the preparation of 2-ethylhexyl acrylate. These octenes are essentially a mixture of isomeric octenes containing 2-ethylhex-2-ene and 3-methylhept-2-ene as main components.

The olefin formed in the oxyester cleavage can be fed continuously or batchwise to the esterification process. Prior removal of the further oxyester cleavage products, i.e. desired ester, starting alcohol and starting acid, is not required but can be carried out. One possibility is to separate the monomeric ester from the mixture vaporizing in the oxyester cleavage and containing the cleavage products and to recycle the remaining cleavage products, i.e. olefin, starting acid and starting alcohol and any further cleavage products to the esterification reactor. Consequently, the monomeric ester is prevented from undergoing a possible further reaction, the recovered starting materials are recycled to the reaction to increase the yield, and the olefin is used as an entraining agent for water of reaction.

The novel process is not restricted to specific α,β-unsaturated carboxylic acids, but monounsaturated or polyunsaturated carboxylic acids and mono- or dicarboxylic acids are suitable. However, the novel process is preferably used in the case of monounsaturated monocarboxylic acids of 3 to 6 carbon atoms and in the case of monounsaturated dicarboxylic acids of 4 to 8 carbon atoms, e.g. acrylic acid, crotonic acid, maleic acid, fumaric acid, itaconic acid, etc. The novel process is particularly advantageously used in the case of acrylic acid and methacrylic acid and in particular for the preparation of 2-ethylhexyl acrylate.

Preferred alkanols are those of 6 to 10 carbon atoms and in particular 2-ethylhexanol (2-ethylhexan-1-ol) or 2-propylheptanol.

It has surprisingly been found that, in spite of the fact that the formation of esters is actually to be expected, olefin isomer mixtures can be used as entraining agents without the esterification and the quality of the desired ester being influenced. A typical example of such an isomer mixture is the stated mixture of isomeric octenes containing 2-ethylhex-2-ene and 3-methylhept-2-ene as main components.

The novel process has the advantage that it is simpler to carry out because no "foreign" entraining agent is used, which introduces an additional component into the system. Rather, an olefin which is in any case formed as a byproduct in the esterification is used as the entraining agent. There is therefore no longer any need specifically to separate off this byproduct, which has a lower boiling point than the desired ester.

The invention is illustrated below with reference to examples, which however serve merely for illustration and in no way are to be understood as imposing any restriction:

The acrylic acid used in the examples below contained essentially the following components:

| | |
|---|---|
| Acrylic acid | 99.7% |
| Acetic acid | 0.10% |
| Propionic acid | 0.04% |
| Diacrylic acid | 0.08% |
| Water | 0.05% |
| MEHQ (hydroquinone monomethyl ether) | 0.02% |

The entraining agent used was an octene mixture which originated from the cleavage of the oxyesters obtained in the preparation of 2-ethylhexyl acrylate. According to gas chromatographic analysis, it contained the following main components:

| | |
|---|---|
| 2-Ethylhex-2-ene | 32% |
| 3-Methylhept-2-ene | 46.7% |
| 5-Methylhept-2-ene | 14.3% |

EXAMPLE 1

336 g of an octene mixture, 238 g of acrylic acid, 1.2 g of phenothiazine and 5.74 g of sulfuric acid (98% strength) were heated in a stirred reactor while stirring and were kept at 114–117° C. for 5 hours. After neutralization of the reaction mixture, no octyl acrylates were detectable by means of gas chromatography.

EXAMPLE 2

A mixture of 238 g of acrylic acid, 390 g of 2-ethylhexanol, 190 g of octene mixture, 0.5 g of phenothiazine and 6.28 g of sulfuric acid (98% strength) was heated to the boil with stirring and under atmospheric pressure in a stirred reactor with attached distillation column (30 cm, 0.5 cm Raschig rings), condensater and water separator and was refluxed for 1.5 hours. The temperature in the reactor increased from 116° C. to 159° C. 50 g of water was separated off via the water separator. The residual acrylic acid content in the reaction product mixture was 3.1%. The acrylic acid conversion was 99% of theory. Gas chromatographic analysis showed that no isomeric octyl esters were formed.

EXAMPLE 3

The procedure was as in Example 2, except that cyclohexane was used instead of the octene mixture. The required reaction time was 2.5 hours. The reaction temperature increased from 98° C. to 114° C. The acrylic acid content of the final mixture was 3.2% and the acrylic acid conversion was 99% of theory.

We claim:

1. A process for the preparation of an ester of an α,β-unsaturated carboxylic acid, which comprises:
   reacting the carboxylic acid with an alcohol which is selected from the group consisting of $C_6$–$C_{12}$-alcohols, cyclopentanol and cyclohexanol, in the presence of an acidic esterification catalyst and of an entraining agent which removes the water of reaction that forms in the esterification, wherein the entraining agent is the unsaturated aliphatic or cycloaliphatic hydrocarbon compound(s) obtained upon removal of water from the alcohol reactant.

2. A process as claimed in claim 1, wherein said unsaturated aliphatic or cycloaliphatic hydrocarbon compound and water are removed from the reaction mixture as a mixture by distillation, water is separated from the mixture and the unsaturated aliphatic or cycloaliphatic hydrocarbon compound is recycled to the esterification process.

3. A process as claimed in claim 1, wherein, after the end of the reaction, the volatile components are separated from the reaction mixture and the remaining, oxyester-containing product is worked up, an aspect of which is the cleavage of oxyesters, thereby resulting in a cleavage product.

4. A process as claimed in claim 1, wherein the alcohol is a linear or branched $C_6$–$C_{10}$-alkanol.

5. A process as claimed in claim 4, wherein the alcohol is 2-ethylhexan-1-ol or 2-propylheptanol.

6. A process as claimed in claim 5, wherein the entraining agent is a mixture of isomeric octenes containing 2-ethylhex-2-ene and 3-methylhept-2-ene as main components.

7. A process as claimed in claim 1, wherein the α,β-unsaturated carboxylic acid is a monounsaturated monocarboxylic acid of 3 to 6 carbon atoms.

8. A process as claimed in claim 1, wherein the α,β-unsaturated carboxylic acid is a monounsaturated dicarboxylic acid of 4 to 8 carbon atoms.

9. A process as claimed in claim 7, wherein the α,β-unsaturated carboxylic acid is acrylic acid or methacrylic acid.

10. A process as claimed in claim 3, wherein, after removal of the ester from the cleavage product, the resulting product is recycled as an entraining agent to the esterification process.

11. A process as claimed in claim 1, wherein the molar ratio of alcohol:acid ranges from 1:0.7 to 1:1.2 and the time of reaction ranges from 1 to 10 hours.

12. A process as claimed in claim 11, wherein the reaction time ranges from 1 to 6 hours.

13. A process as claimed in claim 1, wherein the esterification reaction is conducted at a temperature ranging from about 80 to 160° C.

14. A process as claimed in claim 1, wherein the amount of acid catalyst present ranges from about 0.1 to 10% by weight of the other starting materials.

15. A process as claimed in claim 1, wherein the acid catalyst is a mineral acid, a sulfonic acid or phosphoric acid.

16. A process as claimed in claim 1, wherein the esterification reaction is conducted in the presence of an inhibitor that inhibits the polymerization of unsaturated carboxylic acid reactant.

* * * * *